United States Patent [19]

Acord

[11] 3,960,497

[45] June 1, 1976

[54] CHEMICAL ANALYZER WITH AUTOMATIC CALIBRATION

[75] Inventor: William A. Acord, Claremont, Calif.

[73] Assignee: Beckman Instruments, Inc., Fullerton, Calif.

[22] Filed: Aug. 19, 1975

[21] Appl. No.: 605,947

[52] U.S. Cl. ............................ 23/253 R; 23/230 B; 235/151.13; 235/151.35

[51] Int. Cl.[2] .................... G01N 33/16; G06F 15/42

[58] Field of Search .............. 23/253 R, 259, 230 R, 23/230 B; 235/151.12, 151.35, 151.13

[56] References Cited

UNITED STATES PATENTS

| | | | |
|---|---|---|---|
| 3,535,084 | 10/1970 | Izawa | 23/230 R |
| 3,565,582 | 2/1971 | Young | 23/253 X |
| 3,860,393 | 1/1975 | Campen | 23/253 R |
| 3,874,850 | 4/1975 | Sorensen et al. | 23/253 R |
| 3,907,503 | 9/1975 | Betts et al. | 235/151.35 |

*Primary Examiner*—R. E. Serwin
*Attorney, Agent, or Firm*—R. J. Steinmeyer; R. R. Meads

[57] ABSTRACT

Improved apparatus for automatically calibrating and verifying the calibration of a chemical analyzer of the type which determines the concentration of a component in chemical or biological samples, e.g. concentration of glucose in blood or urine, wherein a sample changer sequentially advances samples into position for analysis. Calibration of the analyzer is performed by measuring a calibration standard of known concentration and generating a conversion factor therefor which converts the measured value of the standard to the known value thereof. Means is provided for storing conversion factors and proper calibration of the analyzer is verified by comparing successive conversion factors. If the compared conversion factors differ by more than a predetermined amount, the sample changer is halted and the calibration standard is remeasured. Measurement of the calibration standard is repeated until either two successive calibration factors are generated which differ by less than the predetermined amount, or until a predetermined number of unsuccessful measurements are made at which time the analyzer is stopped.

3 Claims, 2 Drawing Figures

CHEMICAL ANALYZER WITH AUTOMATIC CALIBRATION

BACKGROUND OF THE INVENTION

1. Field of the Invention

The present invention relates to the calibration of analysis apparatus and, more particularly, to apparatus for automatically calibrating analyzers of the type which measure a particular characteristic of chemical or biological samples.

2. Description of the Prior Art

A number of systems are presently available for automatically analyzing chemical and biological substances to determine, for example, the presence of glucose in serum, plasma, urine, etc., or the presence of urea-nitrogen in serum. In general, such analyzers utilize various sample changing apparatus in order to advance a plurality of samples through the analyzer. Successful operation of the analyzers, of course, requires proper calibration thereof and this is typically performed by measuring calibration standards having known values of the particular characteristic being measured and adjusting the analyzer output until the known value of the calibration standard is displayed.

Unfortunately, the typical calibration procedures presently employed have not proved satisfactory in all respects. For example, many analyzers must be calibrated by hand. Typically, this requires that an operator manually set the instrument in calibrate mode, manually position the calibration standard for measurement, observe the measurement made of the calibration standard, adjust a calibrate knob on the analyzer control panel until the known value of the calibration standard is displayed, and repeatably measure the calibration standard and readjust the calibrate knob until the actual measurements of the calibration standard conform to the known value thereof. Obviously, manual calibration is time consuming and requires the time and attention of a skilled operator.

In one available analyzer, calibration standards are automatically run through the analyzer to calibrate the same. Typically, it takes three to four minutes to run the standards, and once the run has started it cannot be stopped. Thus, if the instrument fails to calibrate properly, it is necessary to wait for the conclusion of the run, and then repeat the entire operation again. This obviously requires excessive operator time and attention and is wasteful of sample and reagents.

In other analyzers, the calibration standard is measured, and if the calibration is unsatisfactory, an indicator or alarm is enabled to attract the attention of an operator who must then spend time troubleshooting or even manually calibrating the analyzer.

SUMMARY OF THE INVENTION

The present invention resides in new and improved apparatus for automatically calibrating chemical analyzers of the type adapted to analyze a plurality of samples which overcomes the disadvantages of the prior calibration procedures. The apparatus of the invention is simple, inexpensive, and commercially practical in construction and is reliable in operation and use.

The analysis apparatus of the invention, in its broader aspects, contemplates sample changing means for advancing samples into position for analysis and for intermittently positioning a calibration standard for measurement of a known characteristic thereof. Means are provided for generating a conversion factor which converts the measured value of the calibration standard to the known value thereof and, in addition, storage means is provided for storing the conversion factors.

In order to verify successful calibration of the analyzer, comparison means are provided for comparing the measured conversion factor with the previously stored factor to determine if the values differ by more than a predetermined amount. If the difference exceeds the predetermined amount, a control signal is generated. Control means respond to this signal to halt the sample changer to maintain the calibration standard in position for analysis, and the calibration standard is remeasured. The calibration standard is measured one or more times until a given number of successive calibration factors are obtained which differ by less than the predetermined amount, thereby verifying proper calibration. After proper calibration, the sample changer advances in normal fashion to position the next sample for analysis.

If no previously stored conversion factor is available, for example when the analyzer is initially turned on, the measured conversion factor is compared with a preset internal conversion factor.

By virtue of the invention, the analyzer automatically and repeatedly performs calibration measurements on a calibration standard if the difference between the initially obtained conversion factors exceeds the predetermined amount. In addition, an operator need not be present during the calibration cycle and, moreover, if an unsatisfactory calibration measurement is obtained, an operator is not needed to manually return the calibration standard into position for remeasurement.

In accordance with a further aspect of the invention, means is provided to count the number of unsatisfactory calibrations, and to shut down the analyzer after a given number of unsuccessful calibrations to prevent the waste of sample and reagent.

DESCRIPTION OF THE PREFERRED EMBODIMENT

Figures 1, 2:
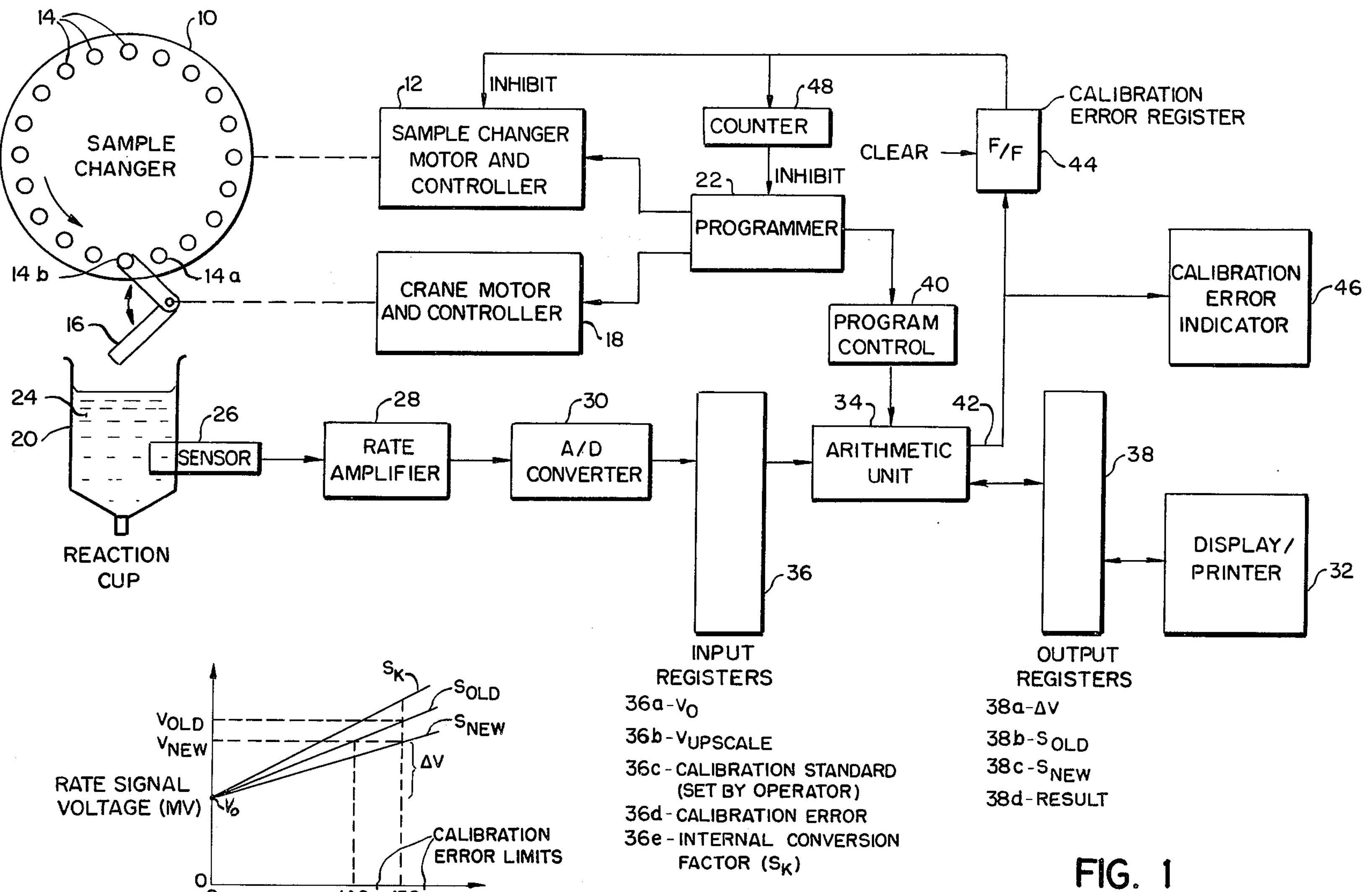
FIG. 1 is a simplified block diagram showing a preferred embodiment of apparatus constructed in accordance with the teachings of the present invention.
FIG. 2 is a graphical representation of curves for converting the voltage output of the rate amplifier in FIG. 1 to concentration units for display.

The calibration apparatus of the invention is described and illustrated as incorporated in analysis apparatus of the type for determining the glucose content of blood, urine, or other samples by reacting the sample with glucose oxidase and measuring the resulting rate of change of oxygen concentration as detailed in U.S. Pat. No. 3,857,771 (Sternberg). However, it should be understood that the principles of the present invention apply to numerous types of analyzers for measuring varied and different characteristics of other sample materials using rate analysis or other techniques, and the present glucose measuring arrangement is given by way of example only. In this respect, reference is made to the following U.S. patents and application, assigned to the assignee of the present invention, describing various other sample handling and analysis apparatus and procedures with which the calibration apparatus of the invention may be incorporated: application Ser. No. 504,390, filed Sept. 9, 1974, by Petersen et al.

titled "Sample Residue Cleaning System for Biological Analyzers"; U.S. Pat. Nos. 3,853,008 (Hoffa); 3,765,841 (Paulson et al.); 3,786,352 (Woods et al.); 3,786,465 (Woods); among others.

As shown in the drawing for purposes of illustration, the calibration apparatus of the invention is embodied in an analyzer including a rotatable sample changer 10 driven by a sample changer motor 12 and adapted to carry a plurality of sample containing vials or tubes 14. A horizontally and vertically movable crane 16 driven by crane motor 18 carries a sample pickup probe (not shown) at one end thereof which is adapted to pick up a given volume of sample from a sample vial 14 and to transfer the sample into a sample reaction cup 20 for analysis. The operational sequence of the sample changer and crane motors 12 and 16 is established and controlled by timing signals from programmer 22 which controls overall operation of the analyzer. The arrangement comprising sample changer 10, crane 16, and programmer 22 is illustrated in a simplified form and, in practice, may take the form illustrated and described in detail in the aforementioned U.S. Pat. No. 3,853,008 or application Ser. No. 504,390.

The sample changer 10 contains a plurality of sample vials 14 which are sequentially advanced into position for analysis. Twenty vials have been illustrated in the figure, including two calibration standards **14*a* and 14*b*** for calibrating the analyzer in a manner discussed subsequently.

Prior to injection of a sample from the crane probe into the reaction cup 20, the cup is automatically filled in a conventional manner with a suitable reagent 24, such as glucose oxidase in the case of rate analysis of blood samples. An oxygen sensor 26 communicates with the interior of the reaction cup and monitors the change in oxygen concentration upon injection of the sample into the reagent. The electrical output from sensor 26, which is proportional to the oxygen concentration, is supplied to a rate amplifier 28 which includes a differentiating circuit for deriving a rate signal indicative of the glucose concentration in the sample. The output of the rate amplifier is, in turn, connected to an analog-to-digital converter 30 to convert the rate signal into digital form for further processing. The arrangement for deriving the rate signal is conventional and may take the form found in the Glucose Analyzer described in Glucose Analyzer Operating Manual 015-083513-F (Nov., 1973) by Beckman Instruments, Inc., Fullerton, Calif., or as illustrated in the aforementioned U.S. Pat. Nos. 3,857,771 or 3,765,841.

Generally speaking, the rate signal from analog-to-digital converter 30 and representing the concentration of glucose or other sample component of interest is processed by the analyzer and displayed by conventional recording means 32. In this regard, the recorder may be calibrated to display glucose concentration in milligrams per deciliter (mg/dl) and may comprise a lighted digital display for displaying results to the operator and a printer for making a permanent record of the results. For example, the recording means 32 may take the form of the recorder found in System TR Analyzer described in Beckman System TR Operating Manual 015-083603-A (Nov., 1973) by Beckman Instruments, Inc., Fullerton, Calif.

More particularly, the rate signal at the output of analog-to-digital converter 30 is processed by an arithmetic unit 34 to convert the signal to a value for display by the recorder 32. In effect, the arithmetic unit multiplies the rate signal value by a conversion factor (derived during calibration of the analyzer) to provide the results for display. FIG. 2 illustrates a family of conversion factors or curves for converting the rate signal voltage output of the converter 30 (millivolts) into units indicative of the concentration (milligrams/deciliter) of the sample component under measure. The conversion curves are illustrated and are identified by their respective slopes $S_K$, $S_{OLD}$, and $S_{NEW}$ to facilitate subsequent discussion of calibration of the analyzer. Beacuse of the nature of the chemical reactions involved in the analyzer of the present type, the conversion curves are linear. As a result each curve can be plotted by determining two points thereof.

The two calibration standards **14*a* and 14*b* are analyzed to derive the two points for plotting a conversion curve. Calibration standard 14*a* is a zero value standard (for example, zero concentration of glucose) and is presented first for analysis by the sample changer 10. The voltage output from converter 30 for the measurement of zero concentration standard 14*a* is indicated as $V_0$ on the vertical axis of the graphical representation in FIG. 2.** Each of the conversion curves crosses the vertical axis at the $V_0$ value.

After the zero value rate signal voltage ($V_0$) is established, the sample changer 10 advances to position the second calibration standard **14*b* for analysis. Calibration standard 14*b* is employed to determine the upscale point of the conversion curve to be derived and thereby establish the actual slope of the conversion curve. In the present example, the concentration of glucose in the calibration standard 14*b* is predetermined and known to be 150 mg/dl. Thus, when the standard 14*b* is measured and a voltage indicative of such measurement is generated ($V_{OLD}$) it is known that the inverse slope of the conversion factor or curve, referred to herein simply as the slope, will be defined by the difference between $V_{OLD}$ and $V_0$ divided into the known concentration of 150 mg/dl. Such a conversion factor or curve is illustrated in FIG. 2** as $S_{OLD}$.

Once a final conversion curve such as $S_{OLD}$, is established for the analyzer, a rate voltage value at the output of converter 30 for a subsequently analyzed sample is converted to mg/dl of glucose by multiplying the rate voltage (corrected to zero by subtracting $V_0$ therefrom) by the slope of the final conversion curve.

In addition to providing automatic calibration as just described, the apparatus of the invention provides automatic calibration verification for the analyzer in two general situations. The first situation is when the analyzer is turned on after having been off, typically the case, for example, when the analyzer is first turned on at the beginning of a day. In the second situation, the analyzer though turned on is calibrated periodically, typically for each new series of sample containing vials 14 loaded into sample changer 10. In this regard, calibration standards **14*a* and 14*b* are analyzed to derive a conversion curve for the analyzer, and the sample vials 14 are sequentially presented for analysis. Thereafter, new sample containing vials 14 are loaded into the sample changer together with the original calibration standards 14*a* and 14*b***. The calibration standards are again analyzed to insure that the analyzer is properly calibrated for the new samples.

In the illustrated form of the invention, an arithmetic unit 34 executes the calculations for deriving the conversion curves and has associated therewith a plurality of conventional input registers **36*a–e*** and a plurality of conventional output registers 38*a–d*. Information stored in the input registers is used by the arithmetic unit 34 for performing calculations, and the results of such calculations are transferred to selected output registers from which they may be retrieved for further processing or displayed by recorder 32.

In this regard and in accordance with well known engineering practices, input register **36*a* is selectively connected to the output of converter 30 to receive and store the zero rate signal $V_0$ derived for the zero concentration calibration standard 14*a*. Input register 36*b* is selectively connected to the output of converter 30 to receive and store the upscale rate signal $V_{UPSCALE}$ derived for calibration standard 14*b* or the sample containing vials 14. Input register 36*c* stores the concentration value of the calibration standard 14*b* (in the present example 150 mg/dl). The value of the standard is loaded into register 36*c* by the operator using thumbwheel switches or the like which may be provided on the analyzer control panel for this purpose. Input register 36*d* stores the value of a maximum predetermined error that may result between the values of successively generated conversion factors without rendering the latter calibration factor unsatisfactory. The predetermined error value may be permanently loaded into register 36*d* during manufacture of the analyzer. For glucose measurement, the predetermined error is 3 percent. Thus, a 3 percent error for a calibration standard having a glucose concentration of 150 mg/dl, would define high and low units for acceptable calibration values of 154.5 mg/dl and 145.5 mg/dl, respectively. Input register 36*e* stores an internal conversion factor $S_K$ which is preferably permanently loaded into register 36*e*** during manufacture of the analyzer. $S_K$ represents the slope of a conversion curve approximating the slope which will be derived by calibrating the analyzer. A typical value for $S_K$ for glucose is 0.87.

Similarly for the output registers and in accordance with well known engineering practices, the register **38*a* is connected to the output of arithmetic unit 34 and receives and stores a difference calculated by unit 34 between $V_{UPSCALE}$ and $V_0$ stored in registers 36*b* and 36*a* (i.e. $\Delta V = V_{UPSCALE} - V_0$). Output registers 38*b*** and *c* receive and store the value of conversion factors designated $S_{OLD}$ and $S_{NEW}$ calculated during calibration of the analyzer. $S_{NEW}$ represents the value of the conversion factor (i.e. the slope of a conversion curve as illustrated in FIG. 2) for a current measurement of upscale calibration standard **14*b*. $S_{OLD}$ represents the value of the conversion factor for the previous measurement of the same standard 14*b*. Output register 38*d* receives and stores a glucose concentration value from analyzing a given sample and is coupled to supply the result to recorder 32** for display.

The arithmetic unit 34 is a conventional four-function calculator for performing addition, subtraction, multiplication, and division. The calculations performed by the arithmetic unit and the transfer of information between registers 34 and 36 and the arithmetic unit is controlled by a program 40 which responds to signals from the analyzer programmer 22, all in a conventional manner. In this regard, each of the input registers **36*a–e* is coupled through gating means, controlled by program control 40, for selectively and individually transferring the information stored in the registers to the arithmetic unit when required. Similarly, the output registers 38*a–d* are coupled through gating means, controlled by program 40,** for selectively and individually transferring the calculations excecuted by the arithmetic unit to the appropriate output register. In addition, the later gating means provides for the selective transfer of information stored in the output registers to the arithmetic unit for further processing.

Gating means is also provided to periodically transfer the contents of output register **38*c* ($S_{NEW}$) to output register 38*b*** ($S_{OLD}$). This is necessary since the value of $S_{NEW}$ calculated for a given calibration measurement becomes $S_{OLD}$ for the next succeeding measurement in a manner discussed subsequently.

In accordance with an important aspect of the invention, calibration measurements on upscale calibration standard **14*b* are performed one or more times, as required, until two successive calibration factors are generated which differ by less than the predetermined calibration error (herein 3 percent) preset in register 36*d*. If the analyzer is operating so that a prior calibration factor $S_{OLD}$ is present in output register 38*b*, then it is possible to recalibrate in a single measurement of the upscale calibration standard 14*b*, assuming that the new calibration factor is found to be within the predetermined error limits. Referring to FIG. 2, assume, for example, that the prior calibration curve is represented by the curve having slope value $S_{OLD}$ of 0.85 and that $V_0$ is 100 mv. Further assume that the present measurement of upscale calibration standard 14*b* provides a rate voltage signal $V_{UPSCALE}$ at the output of converter 30 of 265 mv. Arithmetic unit 34, in the manner previously described, calculates $\Delta V = V_{UPSCALE}$ minus $V_0 = 265 - 100 = 165$ mv and stores this value in register 38*a*. The unit 34 then converts the rate signal to mg/dl of glucose by multiplying ΔV by the slope $S_{OLD}$, i.e. 165 × 0.85 equals 140 mg/dl as illustrated in FIG. 2. Since the actual, known value of calibration standard is 150 mg/dl, the arithmetic unit next computes a new conversion factor or conversion curve so that the 265 mv rate signal will correspond to 150 mg/dl. The new conversion curve has a slope $S_{NEW}$ determined by dividing ΔV into the known glucose concentration, i.e. 165 mv divided into 150 mg/dl to produce a new slope vlaue of approximately 0.9. This new value is stored in register 38*c*.**

The new slope value (0.90) is then compared by arithmetic unit with the prior slope (0.85) to determine if they differ by more than the 3 percent predetermined amount. This is achieved by determining if the absolute value of the function $S_{OLD}/S_{NEW}-1$ exceeds the error limits. For the example given, the error is calculated to be 5.6 percent. Thus, the calibration is unsatisfactory.

After the new slope $S_{NEW}$ has been compared with the prior slope $S_{OLD}$, $S_{NEW}$ is transferred to output register **38*b*** ($S_{OLD}$ is destroyed) and the value of $S_{NEW}$ thus will be used as $S_{OLD}$ when the next calibration is made.

In accordance with a primary aspect of the invention, when the measurement of the calibration standard exceeds the predetermined error limit, a signal is generated from arithmetic unit 34 over conductor 42. This signal enables an error indicator 46 on the analyzer control panel and sets a calibration error register 44 (a conventional flip-flop) the output of which is supplied as an inhibit input to the sample changer motor 12. As a result, when an unsatisfactory calibration value is obtained, the signal supplied from the output of the calibration error register halts sample changer 10. As a result, the calibration standard **14*b* is maintained in position for analysis. Thereafter, calibration standard 14*b* is remeasured and a new rate signal value is derived therefor. A new slope is calculated for the remeasured value of the calibration standard in the manner previously described. This slope is then compared with the slope which had been calculated for the previous measurement. If the difference between these slopes exceeds the predetermined error value, the arithmetic unit 34 again transmits a signal over conductor 42** which inhibits the sample changer, and the calibration standard is remeasured a third time.

If the error between the slopes for the present measurement and the previous measurement at any point is less than the predetermined amount, a satisfactory calibration has been obtained and no inhibit signal is generated over conductor 42. As a result, the sample changer advances to the next sample containing vial 14, and analysis of the samples begins in sequence.

For the situation, previously described, when the analyzer is initially turned on, there is no prior calibration factor stored in output register 38*b*. As a result, in order to make a first conversion of the rate signal from converter 30 to a concentration value, the value of $\Delta V$ is multiplied by the internal conversion factor $S_K$ stored in input register 36*e* to derive the first concentration value. In this regard, $S_K$ functions in the same manner as $S_{OLD}$ as previously described and preferably has a value of about 0.87 for glucose measurements. Then the arithmetic unit calculates the conversion factor ($S_{NEW}$) by dividing the known glucose concentration of 150 mg/dl by $\Delta V$. If $S_{NEW}$ is determined to be within acceptable error limits when comapred with $S_K$ as described above, then $S_{NEW}$ is employed as the conversion factor until the system is again recalibrated.

It should be noted that as long as successive calibration measurements exceed the predetermined error value, the analyzer will continue to remeasure the calibration standard 14*b*. In order to prevent remeasurement indefinitely, a counter 48 is connected between the output of the calibration error register 44 and the programmer 22. After a given number of remeasurements, for example four, the counter supplies an inhibit signal to programmer 22 to shut down the analyzer in order to prevent the waste of sample material and reagents. It should be noted that each time the calibration standard is to be measured, the calibration error register is reset by a clear signal derived from the programmer 22.

From the above, it is apparent that the calibration apparatus of the invention automatically calibrates and verifies the calibration of the analyzer in a novel and unique manner by insuring that two successive calibration measurements differ from one another by less than a predetermined amount. When a calibration standard is analyzed, the apparatus calculates a conversion factor to convert the electrical output signal derived for the standard to units of concentration. The conversion factor is compared with the conversion factor stored from the prior calibration measurement, or with an internal calibration factor if no stored factor is available. If the factors differ by more than the predetermined amount, a control signal is generated to halt the sample changer and the calibration standard is remeasured. The calibration apparatus eliminates the need for manual calibration, constant operator attention, and conserves the use of sample and reagents needed to calibrate the analyzer. Moreover, while a preferred embodiment of the invention has been illustrated and described, it will be apparent that modifications may be made therein without departing from the spirit and scope of the invention as defined by the appended claims.

What is claimed is:

1. Improved calibration apparatus for use in an automatic analyzer of the type which measures a characteristic of a plurality of samples and includes sample changer means adapted to advance said samples in sequential fashion into position for analysis, the sample changer means further adapted to intermittently position for analysis calibration standards having a known predetermined value of said characteristic, the improved calibration apparatus comprising:

measuring means for measuring said characteristic of said calibration standards and generating electrical signals indicative thereof, conversion means responsive to each measurement of a calibration standard for generating a conversion factor which converts each electrical signal to said predetermined value of said calibration standards, storage means for storing said conversion factor, verification means for verifying the calibration of said analyzer upon each analysis of a calibration standard including means for comparing the conversion factor generated for the calibrated standard being measured with the stored conversion factor for the previously analyzed calibration standard and for generating a control signal if the compared conversion factors differ by more than a predetermined amount, sample changer control means responsive to said control signal for halting advancement of the sample changer means to maintain the calibration standard being measured in position for remeasurement, and means for energizing said measuring means to remeasure the calibration standard.

2. The improved calibration apparatus of claim 1 further including means for monitoring the remeasurement of the calibration standard and for stopping operation of said analyzer after a predetermined number of remeasurements.

3. The improved calibration apparatus of claim 1 wherein said verification means compares the conversion factor generated for the calibration standard being measured with a preset conversion factor if no stored conversion factor is available from a previously analyzed calibration standard.

* * * * *